United States Patent [19]

Sipila et al.

[11] Patent Number: 5,107,527
[45] Date of Patent: Apr. 21, 1992

[54] METHOD AND APPARATUS FOR ANALYZING SLUDGY MATERIALS

[75] Inventors: Heikki J. Sipila, Espoo; Marja-Leena Jarvinen; Jouko A. K. Koskinen, both of Helsinki, all of Finland

[73] Assignee: Outokumpu Oy, Helsinki, Finland

[21] Appl. No.: 675,041

[22] Filed: Mar. 25, 1991

[30] Foreign Application Priority Data

Jun. 2, 1986 [FI] Finland ............................ 86 2345

[51] Int. Cl.⁵ .......................................... G01N 23/223
[52] U.S. Cl. ......................................... 378/46; 378/47
[58] Field of Search .................................. 378/46, 47

[56] References Cited

U.S. PATENT DOCUMENTS 4,134,012 1/1979 Smallbone.

FOREIGN PATENT DOCUMENTS 0108447 5/1984 European Pat. Off..
1179894 2/1970 United Kingdom.

OTHER PUBLICATIONS

Nicol, A. W., Editor for "Physicochemical Methods of Mineral Analysis", Chapter 6, pp. 231-247, Plenum, N.Y. and London 1975.

Primary Examiner—Craig E. Church
Attorney, Agent, or Firm—Brooks Haidt Haffner & Delahunty

[57] ABSTRACT

Analyzing sludgy materials by exposing the flowing material in continuous action to x-ray radiation and by measuring the radiation thus created in the said material, according to the invention, the radiation emitted from the material is measured with respect to the intensities of both x-ray fluorescence radiation and x-ray diffraction radiation, and these intensities are combined in order to form a parameter which describes the proportions of the partial components in a given compound combination. Moreover, the detectors employed in the measurement of the radiation intensities are placed at the same cross-sectional plane of the analyzer.

6 Claims, 1 Drawing Sheet

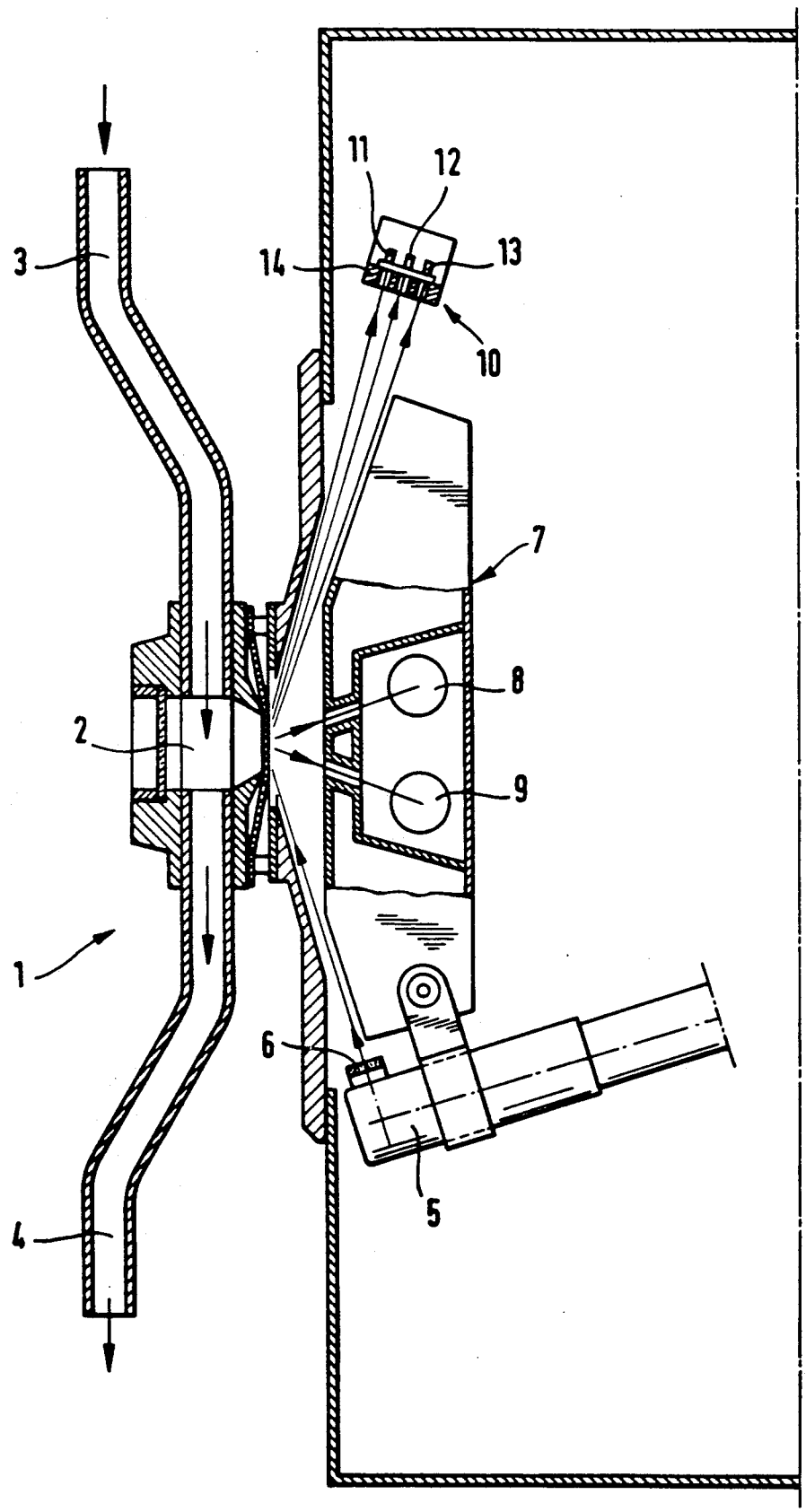

METHOD AND APPARATUS FOR ANALYZING SLUDGY MATERIALS

This application is a continuation of application Ser. No. 461,848, filed Jan. 8, 1990, now abandoned, which is a continuation-in-part of Ser. No. 043,931, filed Apr. 29, 1987, now abandoned.

The present invention relates to a method and apparatus for analyzing sludgy materials by means of exposing them to x-ray radiation in continuous action.

In the prior art there are known several methods where the material under analysis is exposed to continuous-action x-ray radiation. There the analysis is carried out for instance on the basis of the x-ray diffraction obtained from the sample, or by means of the x-ray fluorescence. X-ray fluorescence is normally utilized for defining the content of the elementary components contained in the sludge, whereas x-ray diffraction is utilized for defining the content of the various compounds contained in the sludge. In the prior art methods, however, x-ray diffraction and x-ray fluorescence are measured so that in a case where both measurements are desired, there are installed two separate sets of devices, wherefore the obtained results do not correspond to each other because the measurements have been carried out at different spots of the sample. Consequently the obtained measuring results are not comparable with each other owing to different background radiation, for example.

The prior art technique of x-ray fluorescence analysis is illustrated in U.S. Pat. No. 4,450,576 to Lubecki et al. which describes apparatus for continuous measurement of the elements present in a slurry, but of course, the object of Lubecki et al. is just to measure elements, not compounds. U.S. Pat. No 4,090,073 to DeVilliers et al. illustrates a known technique for x-ray diffraction determination of the concentration of predetermined minerals in a slurry.

The purpose of the present invention is to eliminate some of the drawbacks of the prior art and to achieve an improved method and apparatus for analyzing sludge flows in continuous action, when the sample is exposed to x-ray radiation in order to activate the various components contained therein.

According to the invention, into the effective range of the x-ray radiation produced from an x-ray tube, there is conducted a flow of sludgy material, and the intensities of the essentially simultaneously created x-ray diffraction and x-ray fluorescence are measured by employing such detectors as are suitable for each type of radiation. Thus the radiation from one single x-ray tube can be utilized for measuring both the x-ray diffraction radiation and the x-ray fluorescence radiation of the sludge flow. Consequently, the intensities of both the diffraction and fluorescence radiation can advantageously be measured at an essentially same spot of the continuously proceeding sludge flow.

According to the invention, while measuring both the x-ray diffraction radiation and the x-ray fluorescence radiation caused by a sludgy material at an essentially same spot, the obtained measuring results, i.e. the intensities, can be combined into a parameter which advantageously describes such a proportion of a given partial component, such as an elementary component, which is contained in the particular compound under examination, this compound being formed of the said elementary component. In determining a parameter which describes the proportion of a given partial component, the partial component intensity is the intensity of the x-ray fluorescence, and the x-ray diffraction intensity is employed as the intensity of the whole compound combination. This parameter renders an advantageous result because when the measurement is carried out at an essentially same spot in the sludgy material under measurement, both with the x-ray diffraction and the x-ray fluorescence, the effect of the background radiation caused by various factors is eliminated essentially altogether.

The ratio of the measured intensity of the x-ray fluorescent radiation to the measured intensity of the x-ray diffraction radiation is obtained by electronic means, and this ratio is the parameter which provides the analytical information about the materials present.

The measured x-ray fluorescence radiation indicates the presence of a given element Me. Such element may be present in the form of compounds such as MeO, MeS, $MeS_2$ or the like. The simultaneous measurement of the x-ray diffraction radiation provides the information needed to know what compound of Me is present. If it is determined from the x-ray diffraction intensity that the compound present is, say MeS, then the parameter $$\frac{\text{intensity Me}}{\text{intensity MeS}}$$

provides the information for determining not only the amount of Me present, but also the total amount of MeS.

If the compound present is more complex, such as a compound containing the sulphides of different elements, one can use the term "compound combination" for the complex compound, and one can call the content of a given element a partial component.

Thus the method of the invention consists of continuously exposing a continuous flow of the material to be analyzed to x-ray radiation. This exposure produces x-ray diffraction radiation characteristic of compound combinations present in the material. The x-ray fluorescence radiation which is also produced is characteristic of the elements, or partial components present.

By continuously measuring both the fluorescent and the diffracted radiation; and obtaining the ratio of those two intensities, the proportions of the elements present, and thus the amounts of each can be determined. The composition of the more complex compounds is determined from the intensity ratio of fluorescent to diffracted radiation.

In order to apply the method of the invention, in the detection of the x-ray diffraction radiation caused by the sludgy material under examination there is advantageously employed a multicomponent detector which is provided with a separate detector in the same housing for each separate signal to be measured. Thus an advantageous measurement for each desired component is achieved, because the diffraction angle of the x-ray radiation is a specific quantity pertaining to each different component to be measured.

In the multiwire detector according to the invention which is advantageously suitable for measuring the x-ray diffraction, there is provided a high voltage source and a gas filling common for all subdetectors, whereas the front amplifiers in the subdetectors are separate and depend on the volume of the signal. In addition to this, the multiwire detector according to the invention is provided with a perforated plate placed in front of the plurality of the separate subdetectors, so that the said plate advantageously guides the desired diffraction signals into the subdetector designed for each particular component.

While applying the method of the invention in the measurement of x-ray fluorescence radiation, there is advantageously used a detector operated with energy dispersion, such a detector being for instance a proportional counter or a semiconductor detector. The measurement of the desired x-ray fluorescence signals can also be carried out advantageously with crystal spectrometers provided with fixed channels.

Because in the method of the invention the x-ray diffraction and x-ray fluorescence radiated from the sludgy material are both advantageously measured at the same spot, the detectors detecting both types of radiation can be placed advantageously on essentially the same cross-sectional surface of the analyzer.

In the following the invention is explained in more detail with reference to the appended drawing which is an illustration of a preferred embodiment of the invention seen in a partial side-view elevation.

According to the illustration, the continuous-action x-ray analyzer 1 of the invention is provided with a measuring cell 2, whereinto the sludgy material to be analyzed is conducted via the inlet pipe 3 and further out of the cell 2 via the outlet pipe 4. In the analyzer 1, there is installed an x-ray tube 5, and the radiation emitted therefrom and filtered through the filter 6 is employed for irradiating the sludgy material which enters the measuring cell 2. In order to detect the x-ray fluorescence now created in the exposure, there are arranged detectors 8, 9 near the center part of the collimator 7.

In the measurement of the x-ray diffraction radiated from the sludgy material, there is employed a multiwire detector 10. The detector 10 is, according to the drawing, composed of three subdetectors 11, 12 and 13, each designed for one particular component, and in front of the said detectors there is placed a perforated plate 14, which lets only such x-ray diffraction radiation which is scattered at a desired angle enter through the separate holes.

What is claimed is:

1. A method for analyzing sludgy materials by conducting the material to a measuring cell through an inlet pipe, continuously exposing a continuous flow of the sludgy material containing various compounds and elements in the measuring cell to x-ray radiation to activate x-ray diffraction radiation characteristic of compound combinations present in the sludgy material and x-ray fluorescence radiation characteristic of elementary components present in the sludgy material, measuring such x-ray fluorescence and x-ray diffraction radiations essentially simultaneously to obtain intensity measurements and using ratio of said intensity measurements to form a parameter which describes the proportions of elementary components in a given compound combination.

2. The method of claim 1 wherein the x-ray fluorescence intensity measurement represents elementary component intensity and the x-ray diffraction intensity measurement represents the given compound combination intensity in formation of said parameter.

3. The method of claim 1 or 2, including measuring said x-ray fluorescence radiation and said x-ray diffraction radiation at essentially the same spot in the flowing sludgy material.

4. Apparatus for analyzing sludgy materials by continuously exposing continuously flowing sludgy material containing various compounds and elementary components to x-ray radiation, comprising a measuring cell, inlet and outlet pipe means for conducting sludgy material to and through said measuring cell, an x-ray source for irradiating sludgy material in the measuring cell and detectors for detecting x-ray fluorescence and x-ray diffraction radiation, said detector for detecting x-ray diffraction radiation being a multiwire detector which has a separate detector for each of several x-ray diffraction intensities measured and including a perforated plate in front of the multiwire detector for letting through to the detectors radiation diffracted at different angles, said detectors being located on the same cross-sectional surface of said apparatus, and further comprising means for determining a ratio of the intensity of the detected x-ray fluorescent radiation to the intensity of the detected x-ray diffraction radiation to determine the proportions of elementary components in said sludgy material.

5. The apparatus of claim 4, wherein the x-ray fluorescence detector is a proportional counter.

6. The apparatus of claim 4, wherein the x-ray fluorescence detector is a semiconductor detector.

* * * * *